United States Patent [19]
Jhuboo et al.

[11] Patent Number: 5,501,665
[45] Date of Patent: Mar. 26, 1996

[54] PROCESS AND DEVICE FOR DETECTION OF OBSTRUCTIONS IN A PERFUSION LINE

[75] Inventors: Abdel-Nasser Jhuboo, St. Etienne de St. Geoirs; Pierre Rebours, Voiron, both of France

[73] Assignee: Becton Dickinson and Company, Franklin Lakes, N.J.

[21] Appl. No.: 276,300

[22] Filed: Jul. 18, 1994

[30] Foreign Application Priority Data

Sep. 30, 1993 [FR] France .................................. 93 11654

[51] Int. Cl.$^6$ .................................................. A61M 31/00
[52] U.S. Cl. ................................................ 604/65
[58] Field of Search ............................. 604/30–34, 48, 604/49, 53, 65–67, 154, 250–256

Primary Examiner—C. Fred Rosenbaum
Assistant Examiner—Manual Mendez
Attorney, Agent, or Firm—Alan W. Fiedler

[57] ABSTRACT

A process for detecting obstructions in a perfusion line, wherein a programmable syringe pump uses a selected gradient constant and first and second pressure measurements from the perfusion line to determine whether an obstruction has occurred in the perfusion line.

22 Claims, 14 Drawing Sheets

PROCESS AND DEVICE FOR DETECTION OF OBSTRUCTIONS IN A PERFUSION LINE

The present invention concerns in general the detection of obstructions in a perfusion line. In particular, the invention concerns a programmable syringe pump, which uses an algorithm to determine whether an obstruction exists in the perfusion line.

A syringe pump is a device for pumping a fluid from a syringe into the body of a patient. The syringe is disposed in the pump and connected to the patient by means of a perfusion line. During the perfusion of a medication into the body of a patient, it is possible that an obstruction may be produced in the perfusion line. Such a state may cause injury to the patient if it is not detected.

Syringe pumps generally detect obstructions by monitoring the pressure on the syringe plunger to detect obstructions. Different processes are used to achieve this goal. The simplest process involves monitoring the pressure in the perfusion line at regular time intervals. When the pressure exceeds a predetermined level, an alarm signal is generated. To minimize false alarms, the pressure at which the alarm is triggered is fixed at a level much higher than the normal line pressure. The use of this process requires a relatively long time interval to detect an obstruction, since the pressure in the line must reach the alarm level before an obstruction is detected.

According to a second process of the prior art, rather than the instantaneous pressure in the perfusion line, the mean pressure is measured during a time span after a predetermined stabilization time (cf. FIG. 1). The alarm level is fixed at a level close to the mean line pressure. This process can trigger false alarms caused by brief increases in pressure above the alarm limit.

The present invention has as its object a process for the detection of obstructions in a perfusion line, the process being characterized by the fact that it comprises steps consisting of selecting a gradient constant; measuring an initial pressure in the perfusion line; measuring a second pressure in the perfusion line after a time interval; subtracting the first pressure from the second pressure to obtain a first pressure difference; comparing the first pressure difference to the gradient constant; and generating a signal if the first pressure difference exceeds or is equal to the gradient constant.

Advantageously, the process according to the invention comprises the steps consisting of measuring a second pressure in the perfusion line after an initial time interval; subtracting the first pressure from the second pressure to obtain a first pressure difference; comparing the first pressure difference to the gradient constant; measuring the third pressure after a second time interval; subtracting the third pressure to obtain a second pressure difference; comparing the second pressure difference to the gradient constant; and generating a signal if the first pressure difference and the second pressure difference exceed the gradient constant.

According to other advantageous characteristics of the invention:

the gradient constant is a function of the flow rate;

the gradient constant is directly proportional to the flow rate;

the first and second time intervals are essentially equal;

the process comprises steps consisting of comparing the first pressure difference to the gradient constant, of comparing the second pressure difference to the gradient constant, and of generating the signal only if the first and second pressure differences both exceed the gradient constant;

the process also comprises an automatic modification step where the time interval is changed in a manner inversely proportional to the flow rate of the fluid in the perfusion line;

the process comprises an automatic adjustment step where the time interval is adjusted in response to a noise on the perfusion line;

the time interval is automatically increased to reduce the influence of noise on the perfusion line;

the process also comprises a step where the first pressure difference is compared to a constant and the first time interval is adjusted if the first pressure difference exceeds the constant;

the adjustment step comprises an increase in the first time interval;

the constant is deduced from the gradient constant;

the constant is the gradient constant multiplied by a scale change factor;

the scale change factor is deduced empirically;

the process comprises a step where the first pressure difference is compared to a constant and where the time interval is automatically adjusted if the first pressure difference is less than the constant;

the adjustment step comprises a reduction of the time interval;

the process comprises a step featuring the optimization of the first time interval;

the optimization step uses a process operating by dichotomy;

the optimization step comprises iteration steps to establish an initial time interval by comparing the initial time difference to a constant;

the optimization step comprises a step where the time interval is increased if the absolute value of the first pressure difference exceeds a first constant and where the time interval is reduced if the absolute value of the first pressure difference is less than a second constant;

the time interval increase step comprises the doubling of the first time interval;

the time interval reduction step comprises a step where the first time interval is reduced by two.

Figure 1:
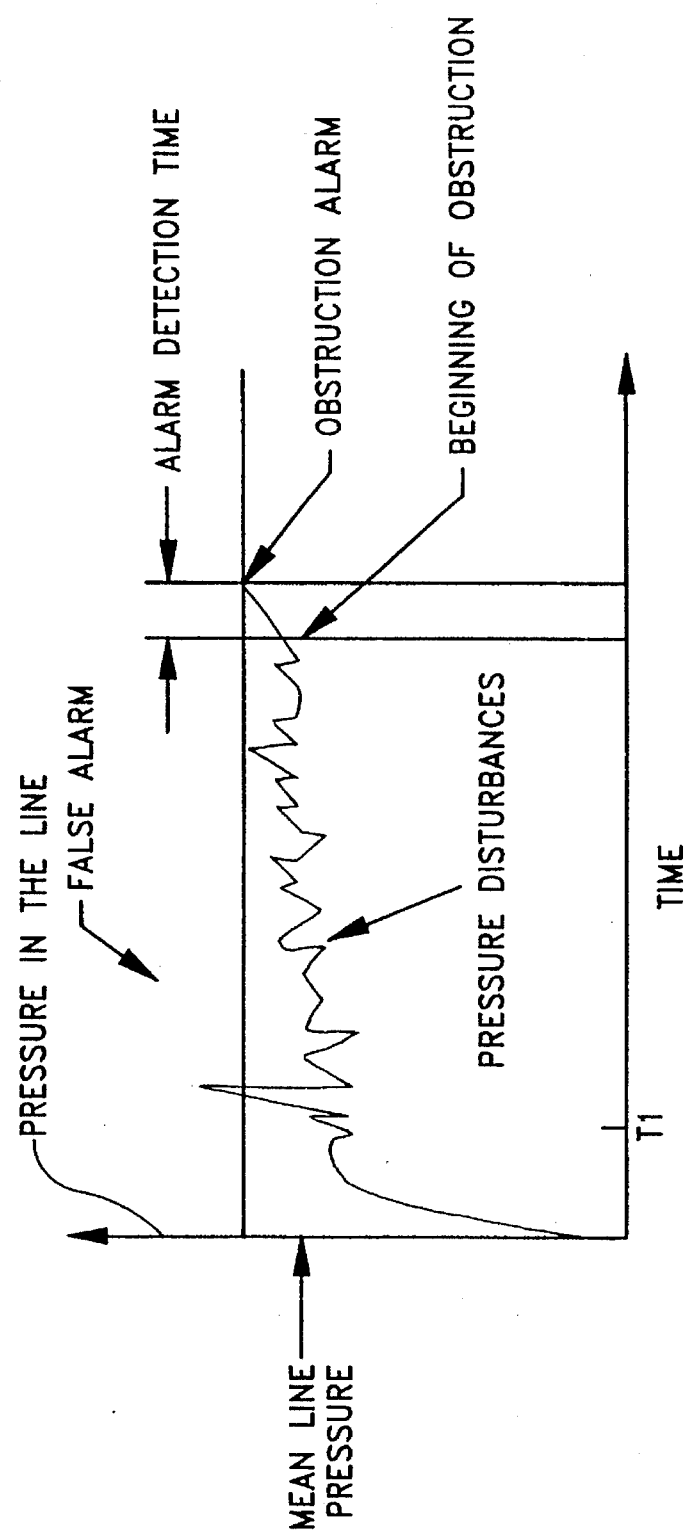
FIG. 1 is a graph of the pressure as a function of the time using the process from the prior art.
Figure 2:
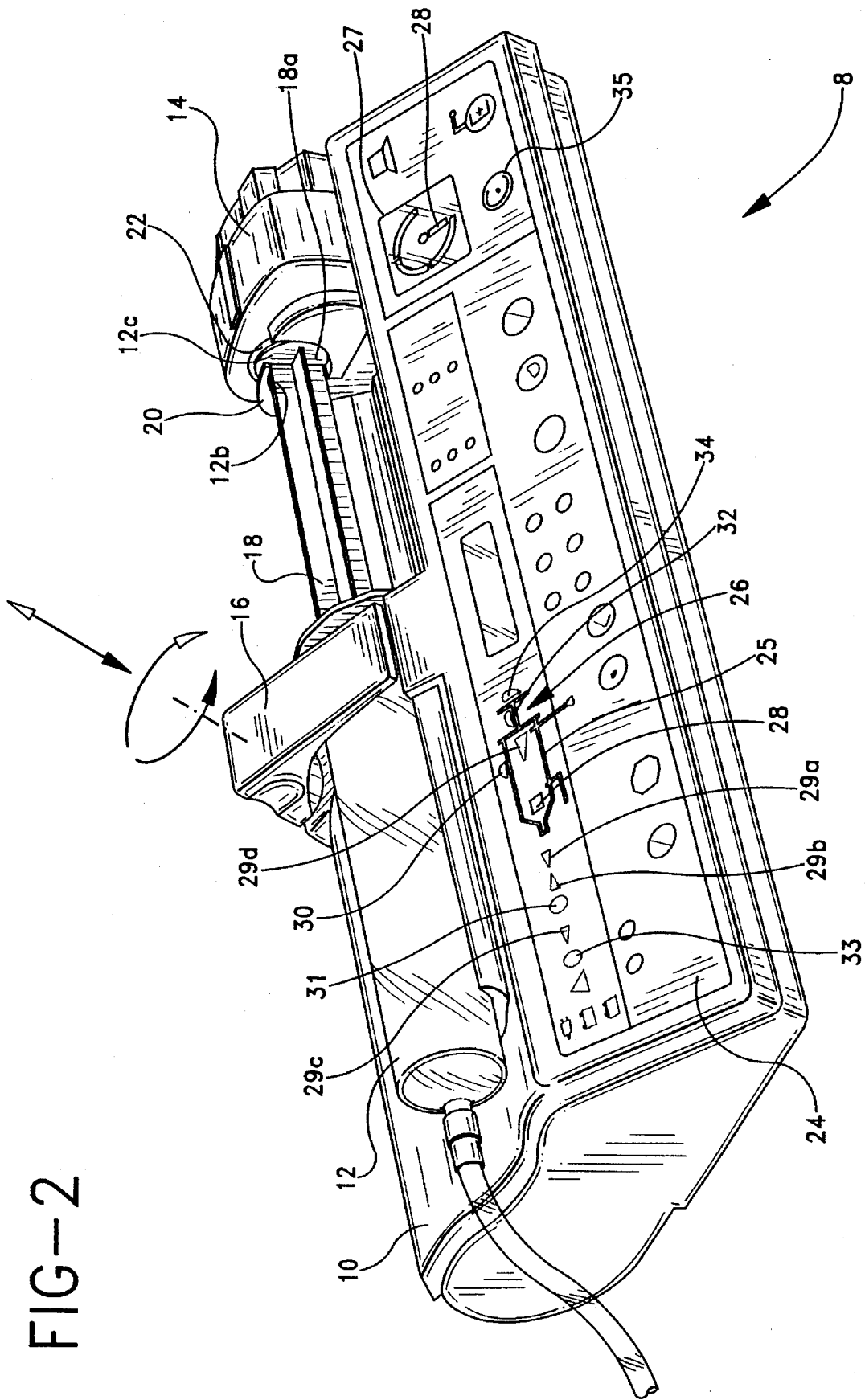
FIG. 2 is a perspective view of a syringe pump incorporating the invention.

A syringe pump 8 incorporating the invention is depicted in FIG. 2. A case 10 holds a syringe 12, a pushing mechanism 14, and a syringe clip 16. The syringe clip 16 holds syringe 12 in position on case 10. Plunger 18 of syringe 12 is pushed by a pushing mechanism 14 which is driven by an electric motor via a feed screw (cf. FIG. 2).

Pushing mechanism 14 is equipped with an antisiphon stop device 20 which cooperates with a flange 18a of plunger 18, thereby preventing plunger 18 from moving independently of pushing mechanism 14. Pushing mechanism 14 is also equipped with a pressure plate 22 to push directly against flange 18a, thereby pumping fluid from syringe 12.

Figure 3:
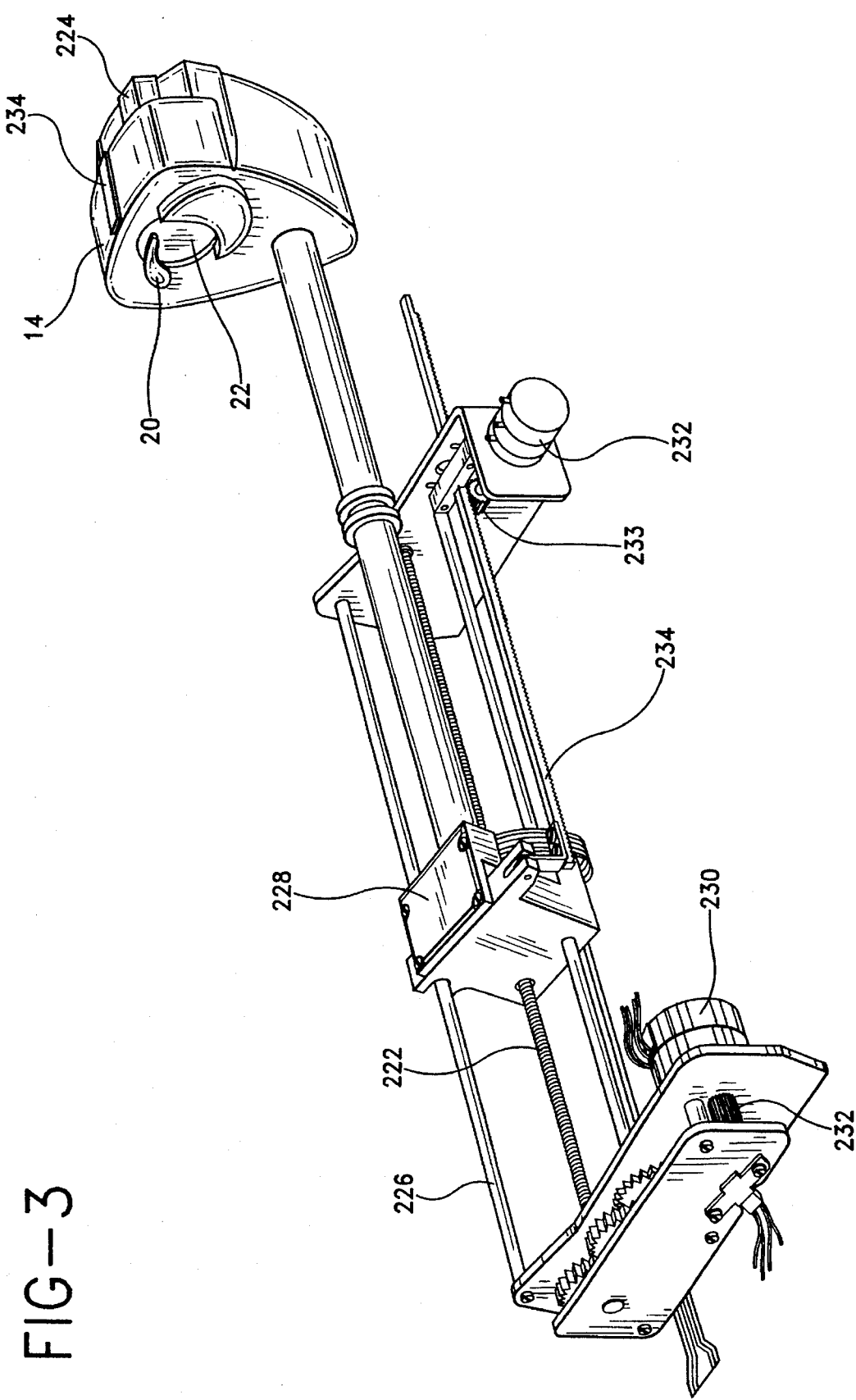
FIG. 3 is a perspective view of the syringe pump drive mechanism.

FIG. 3 represents the frame and the mechanical constituents of the pump 8. Frame 226 has a motor 230 and a feed screw 222. Motor 230 drives the feed screw 222 via the gear train 232. Pushing mechanism 14 is driven by the interaction of plunger block 228 with feed screw 222. The plunger block contains half-nuts which interact with feed screw 222.

Figure 4:
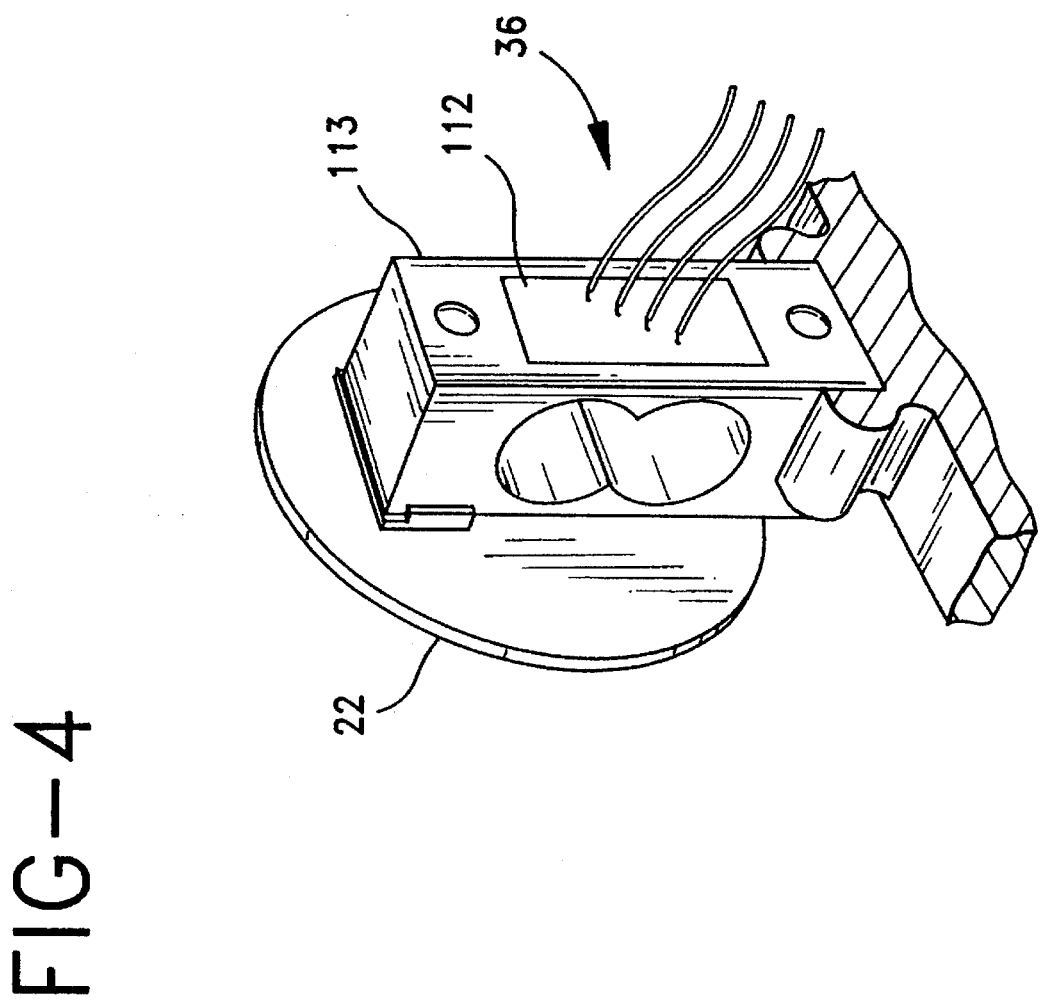
FIG. 4 is a perspective view of the pushing mechanism disk and of the force transducer.

FIG. 4 represents in greater detail the force transducer 36. The force transducer 36 consists of four strain gauges mounted on a Wheatstone bridge. The bridge has an impedance of 350 ohms or 1 Kohm with a tolerance of ±15%. The force measurement range is 0 to 150 N. The sensitivity of the bridge is 1.7 mV/V to 2.4 mV/V under a load of 150 N at 20° C. The bridge is powered intermittently under the control of a microprocessor 46 (line CDANA on FIGS. 6a and 6d) to economize energy.

As may be seen on FIG. 4, the strain gauges 112 are fastened to a bar 113. When a force is applied to the pressure plate 22, the bar 113 bends, causing a distortion of the strain gauges 112, which deliver an output signal 60.

Figure 5:
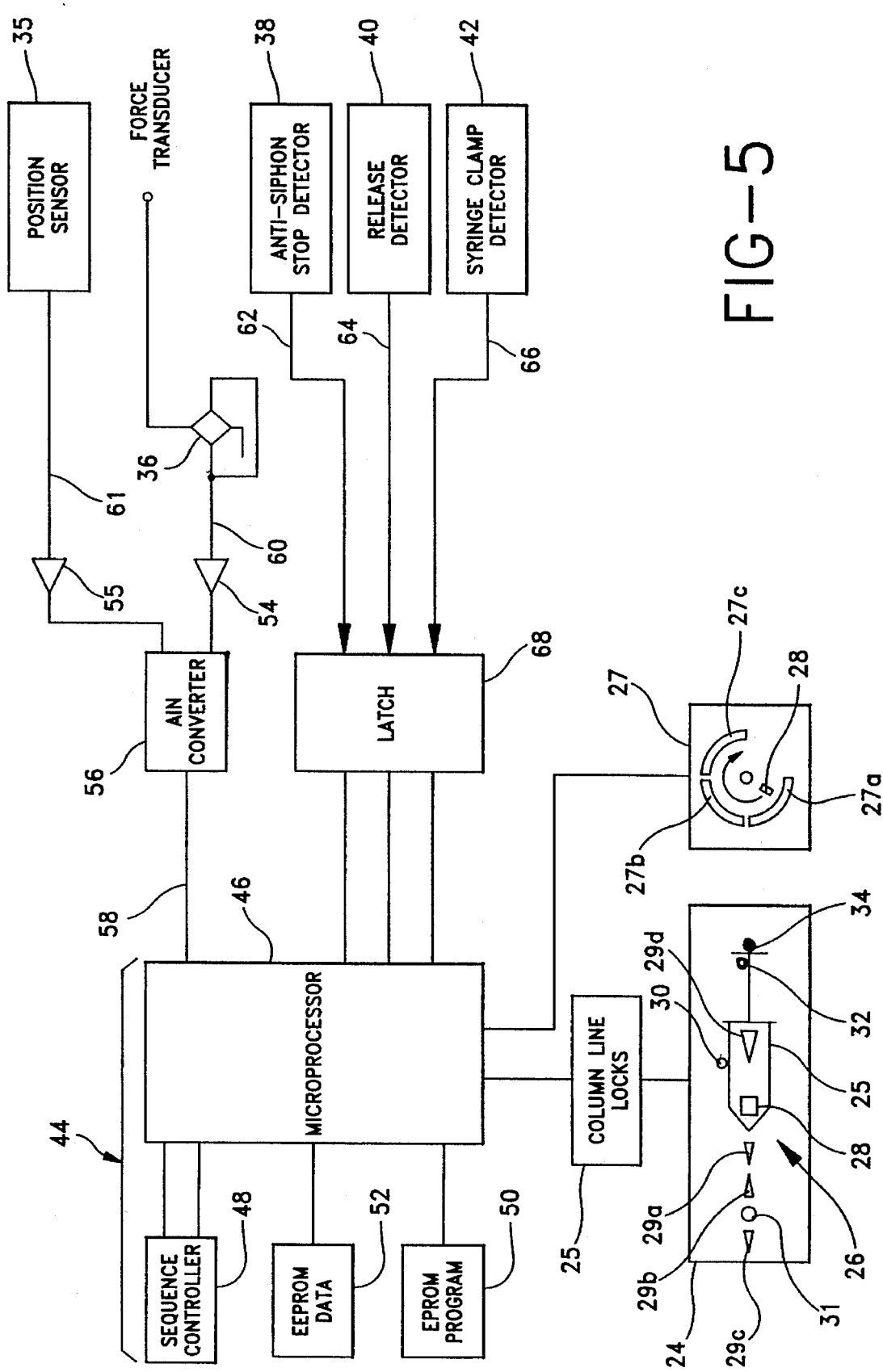
FIG. 5 is a synoptic diagram of the electronic components of the invention.
Figure 6A:
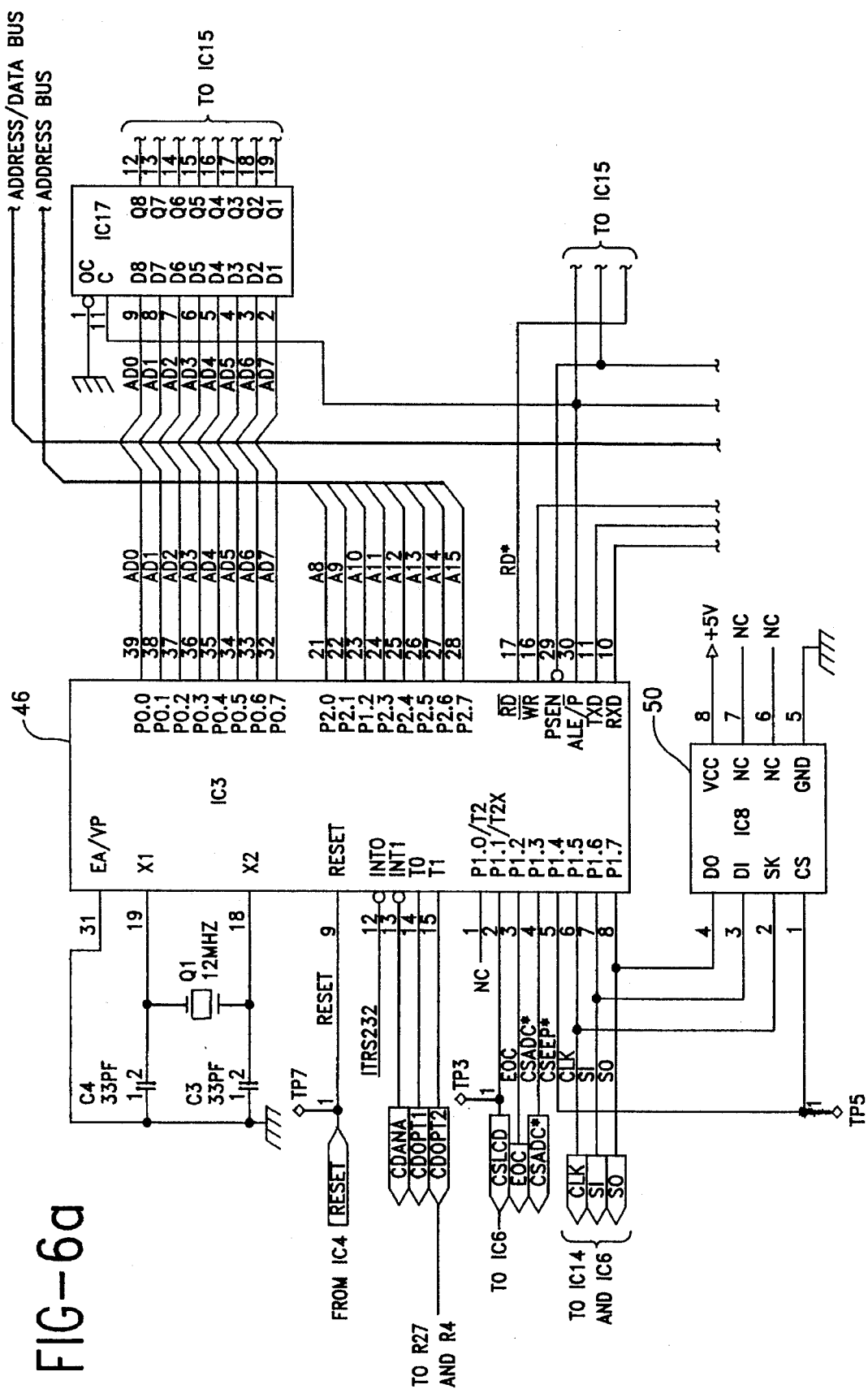
FIGS. 6a to 6e are diagrams of the principal electronic components of the invention.
Figure 6B:
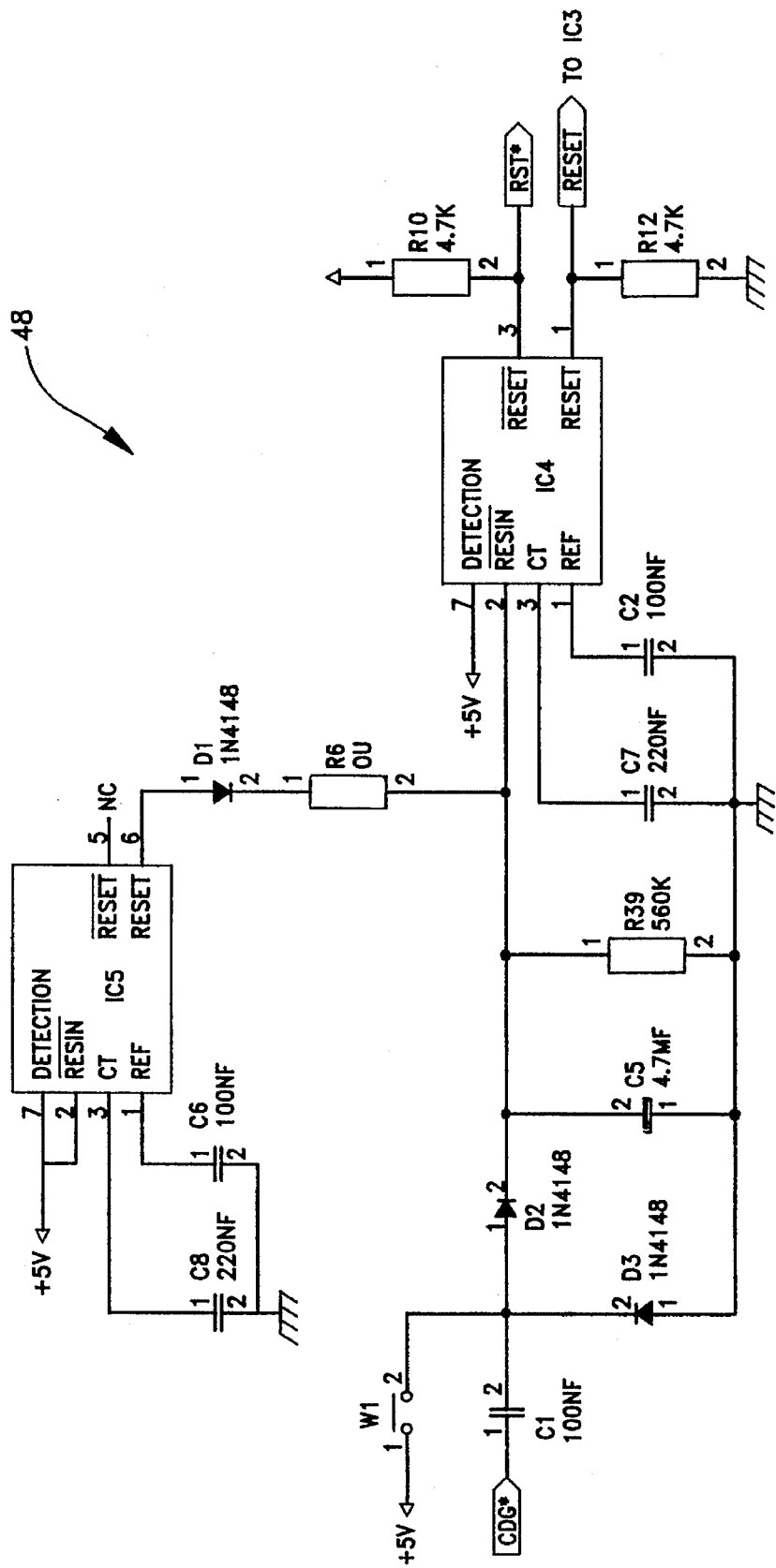
Figure 6C:
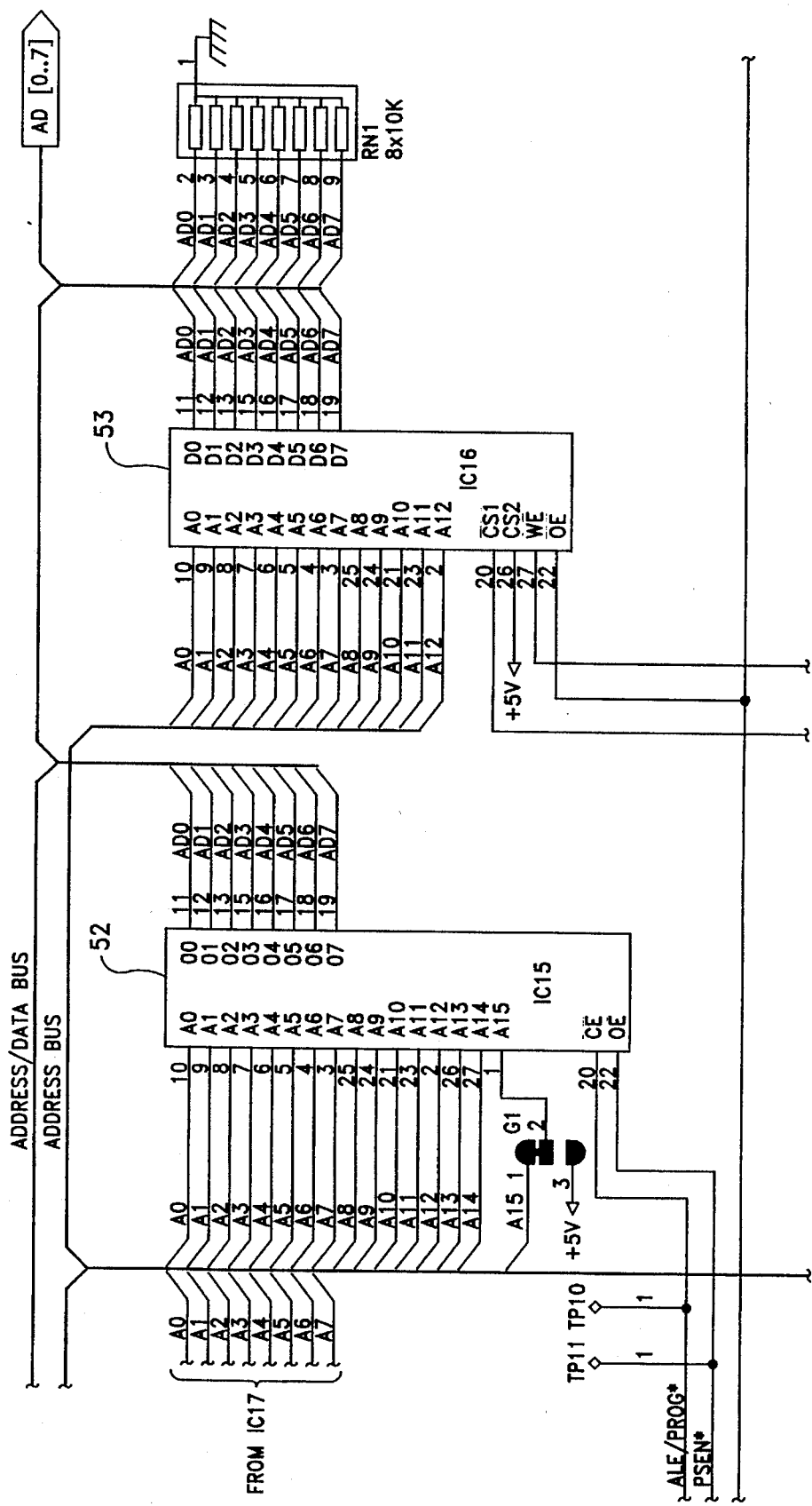
Figure 6D:
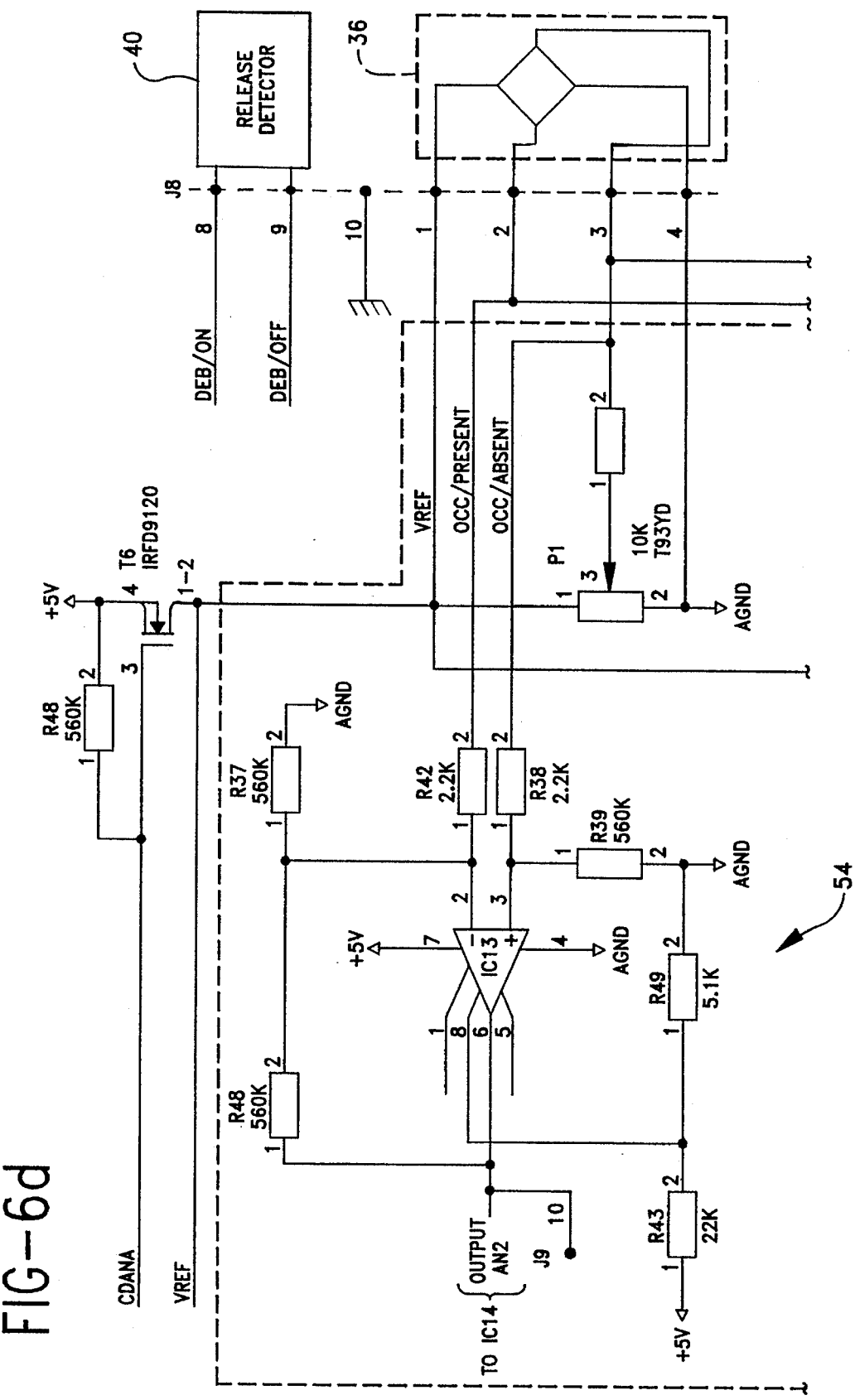

FIG. 5 is a synoptic diagram representing the principal electronic components of the invention. Transducers are provided to detect different parameters of the syringe pump which are displayed on a panel 24. The transducers are: the force transducer 36, the antisiphon stop device detector 38, the release detector 40, and the syringe clip detector 42. The output signals from these transducers 60, 62, 64, and 66 respectively are applied to a central treatment unit 44 by different signal treatment modules. Diagrams of the different electronic modules are depicted in FIGS. 6a–c. The values and the types of the components are indicated on the diagrams.

The output signal 60 from force transducer 36 is applied to the processing module 54 (FIG. 6d) and then to an analog-to-digital converter 56 which converts the process output signal from the force detector 36 into the serial output signal 58. The serial output signal 58 is then applied to the input 60 of the microprocessor 46.

The central treatment unit 44 consists of the microprocessor 46 (FIG. 6a) with a random access memory 53 (FIG. 6a), a sequence controller 48 (FIG. 6b), an electrically programmable read-only memory 50 (FIG. 6a), and an electrically-erasable programmable read-only memory 52 (FIG. 6c). The sequence controller 48 monitors the microprocessor 46 to ensure that it functions correctly. The electrically-erasable programmable read-only memory 52 contains data concerning the syringe parameters used in the pump. The electrically programmable read-only memory 50 contains a software program which controls the operation of the syringe pump.

Figure 6E:
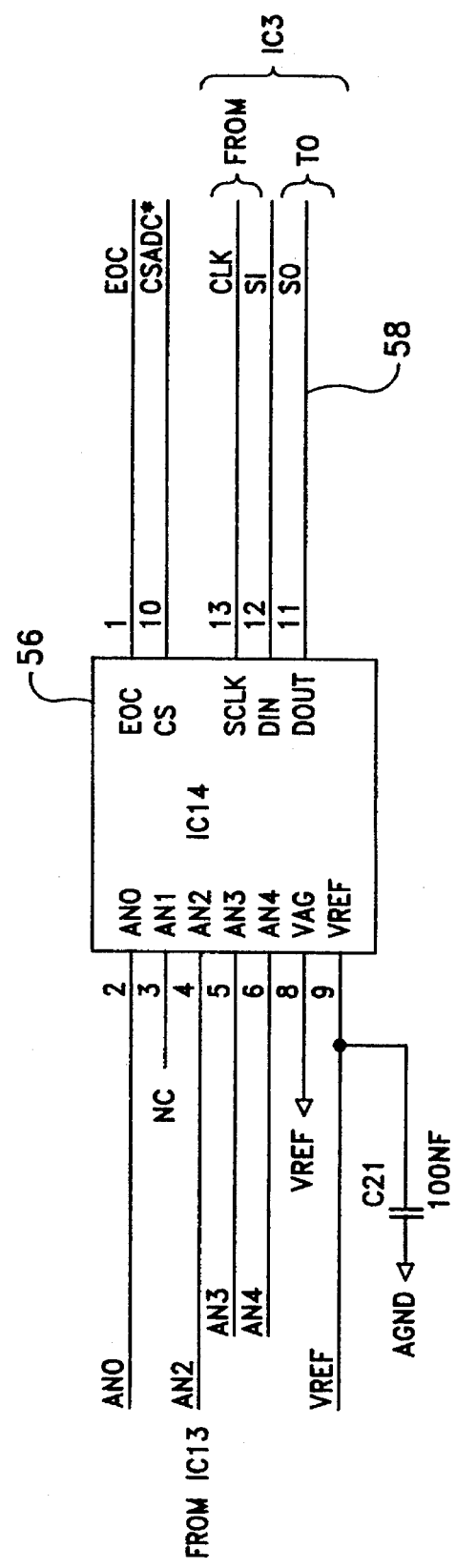

The output signal from the force transducer 36 is processed by a signal processing 54 (FIG. 6d), which converts the output signal from the force transducer 36 into an appropriate form for application to an analog-to-digital converter 56 (FIG. 6e). The analog-to-digital converter 56 digitizes the analog output signal and delivers a serial output signal 58 which is in turn applied at the input connection point 60 of the microprocessor 46.

The electrically programmable read-only memory 50 has a software program for the microprocessor 46 which calculates the pressure inside the syringe 12 continuously, since the force on the plunger 18 is measured by the force transducer 36. Certain parameters which are used by the program to calculate the pressure in the syringe are stored in the electrically erasable programmable read-only memory 52. Since the syringe pump 8 is programmable to receive different types of syringes, a set of parameters for each type of syringe is stored in the electrically erasable programmable read-only memory 52.

The parameters stored in the electrically erasable programmable read-only memory 52 include:

Ff=mean force of friction between the syringe plunger and the barrel of the syringe at zero pressure (atmospheric).

Pc=the pressure in the syringe when a calibration force is applied to the plunger. The calibration force is typically 50 N and produces a Pc value of approximately 0.7 bar, a common pressure threshold.

Fc=the force with which the plunger is charged to obtain a pressure of Pc in the syringe.

The program in the electrically programmable read-only memory 50 is used by the microprocessor 46 to calculate the pressure in the syringe. The microprocessor 46 then compares the pressure calculated at a pressure value among the values stored in the electrically erasable programmable read-only memory 52 for this syringe. If the calculated pressure exceeds the stored pressure, an obstruction alarm is generated by the microprocessor 46.

The algorithm to calculate the pressure in the syringe is:

$$P = \frac{(F - Ff)}{Fc - Ff} \cdot Pc$$

where F is the force measured by the force transducer 36 and Fc, Ff, and Pc are the parameters described above.

Figure 7:
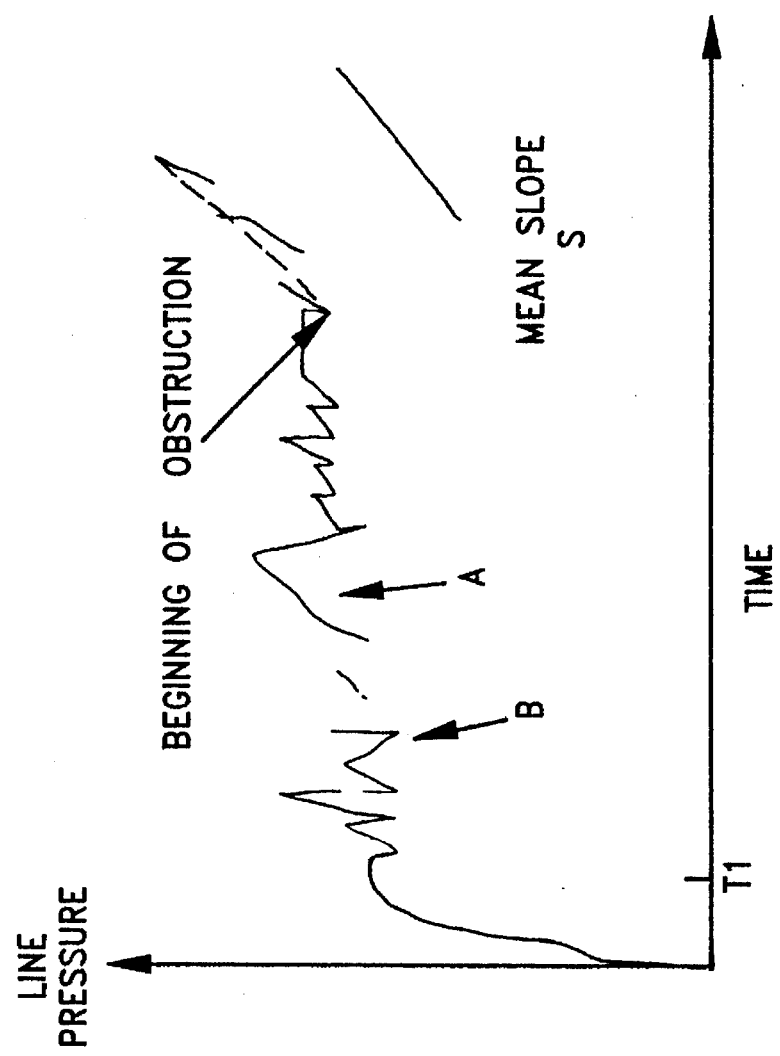
FIG. 7 is a graph of the pressure as a function of time using the present invention.

If an obstruction is produced in the fluid pathway, the pressure in the fluid pathway will increase. If the motor 230 continues to drive the pushing mechanism 14, the pressure in the fluid pathway will increase over time. FIG. 7 shows a graph of the pressure in the fluid line as a function of the time. During perfusion, the pressure in the fluid line may be subject to disturbances which are not caused by an obstruction. For example, since the friction force between the syringe stop 12 and the inner wall of the syringe varies nonlinearly, a disturbance in pressure (designated "A" on FIG. 7) may occur. Disturbances may also be produced by the presence of other perfusion devices on the line. Such a disturbance is designated by "B" on FIG. 7.

An obstruction is detected by determining the "S" gradient of the pressure-time curve depicted in FIG. 7 and by comparing it to a predetermined gradient. The pressure in the fluid line is measured in the manner described above.

Figure 8:
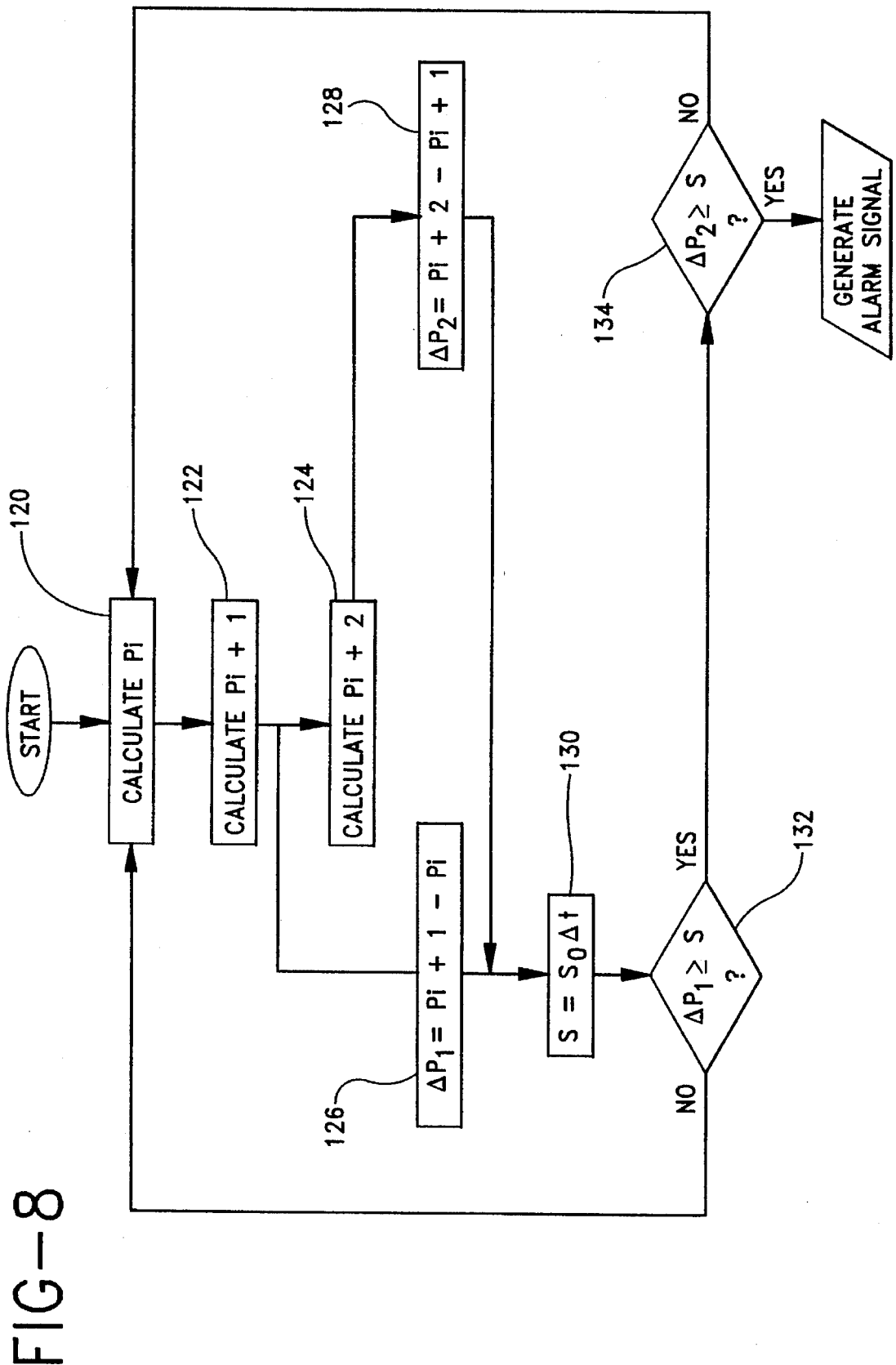
FIG. 8 is a flow chart illustrating the process of detecting obstructions.

The following pressure measurements are done at the following time intervals:

$P_i$=mean pressure in the interval $[t_i; t_i \Delta t]$ $P_{i+1}$=mean pressure during the interval $[t_i + \Delta t; t_i + 2\Delta t]$ $P_{i+2}$=mean pressure during the interval $[t_i + 2\Delta t; t_i + 3\Delta t]$ These steps are represented as steps 120, 122, and 124 in the flow chart in FIG. 8.

The gradient of the pressure/time curve in FIG. 7 may be defined in a general manner by:

$$S = \Delta P / \Delta t$$

where P is the increase in pressure in the perfusion line in a given time interval $\Delta t$. The amplitude of S is proportional to the flow rate of the liquids in the fluid line.

The gradient is measured as follows. The microprocessor 46 is programmed to calculate the difference between the pressures at the end of succeeding time intervals and then compares it to a constant deduced from a number representative of an acceptable predetermined gradient of the pressure/time curve ($S_0$) and of the amplitude of the time interval $\Delta t$.

Thus, the microprocessor subtracts $P_i$ from $P_{i+1}$ and compares the result to $S_0 \Delta t$. Cf. steps 126, 130, and 132 in FIG. 6. If $\Delta P_1 = P_{i+1} - P_i$ is greater than $S_0 \Delta t$, the gradient of the pressure/time curve is above a permissible level. This means in turn that there is an obstruction in the fluid line, and an alarm signal is generated to light an indicator light 29b (step 134 on FIG. 8). Another comparison can be made by subtracting $P_{i+1}$ from $P_{i+2}$ and by comparing the result $\Delta P_2$ to $S_0 \Delta t$ (steps 128, 130, and 134). It is possible to use only the first comparison ("if $\Delta P_1 \geq S_0 \Delta t$") or, preferably, the first in combination with the second comparison ("if $\Delta P_2 \geq S_0 \Delta t$"). In other words, an obstruction signal will be generated only if $\Delta P_1$ and $\Delta P_2$ are both greater than or equal to $S_0 \Delta t$.

$S_0$ is deduced experimentally by measuring the gradients of the pressure/time curve with obstructions found in the fluid line and different flow rates. $S_0$ is directly proportional to the flow rate. The microprocessor 46 is programmed to permit different values of $S_0$ to be chosen before or during the perfusion process. Using the process described above, even if $S_0$ is low, it is possible to detect a partial obstruction, since it is the pressure variation speed rather than the pressure itself that is measured.

The time interval $\Delta t$ is adjusted automatically during a perfusion. The time interval $\Delta t$ is inversely proportional to the flow rate r. The flow rate r may be chosen by the user and programmed into the syringe pump 8. The magnitude of $\Delta t$ is also a function of the quantity of noise in the system. If $\Delta t$ is small, the system will be sensitive to rapid pressure variations.

If the system has noise, $\Delta t$ must be large and the system will be less sensitive to pressure variations. If the system is less subject to noise, $\Delta t$ can be small, making the system react faster to an obstruction. A description follows below of the optimization process of $\Delta t$, the time during which the gradient of the pressure/time curve is measured.

The initial value of $\Delta t$, $\Delta t_0$ is inversely proportional to the perfusion speed r. For example, for r=1 ml per hour, $\Delta t_0 = 1$ minute. The value of $\Delta t_0$ is determined empirically. Having chosen an initial value for $\Delta t$, it must first be established whether $\Delta t$ should be increased or decreased.

Considering the time interval $[t_1, t_i + \Delta t]$, if $\Delta P_1 > K_1 S_0 \Delta t$, $\Delta t$ must be increased, since the pressure increases rapidly and the system is likely to be subject to noise;

if $\Delta P_1 < K_2 S_0 \Delta t$, $\Delta t$ should be decreased, since the pressure increases less rapidly, and the system will be less subject to noise.

In the preferred exemplified embodiment, the constants $K_1$ and $K_2$ are as follows: $K_1 = \frac{1}{4}$; $K_2 = \frac{1}{8}$ and are deduced empirically.

Figure 9:
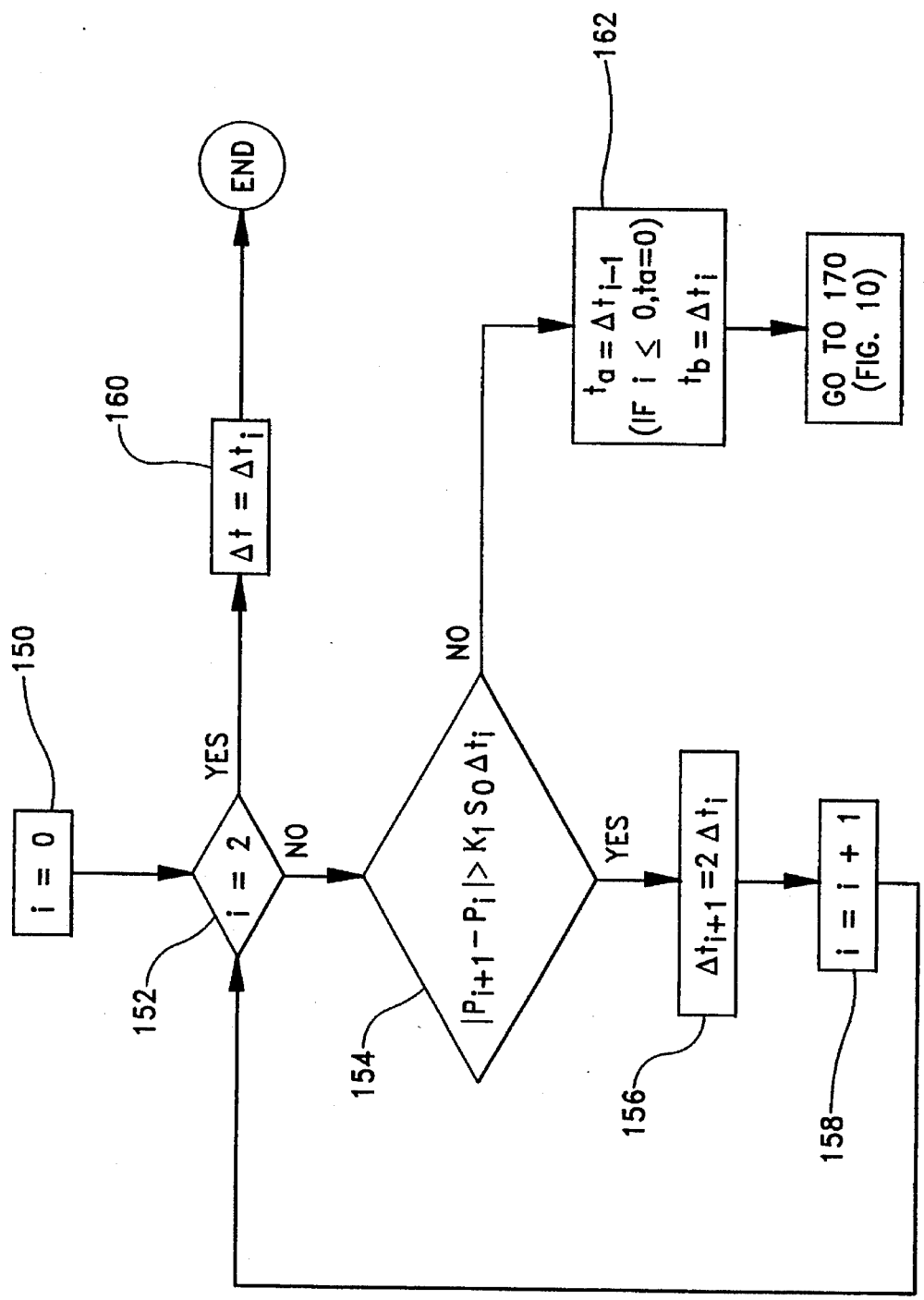
FIG. 9 is a flow chart illustrating the process of determination of the time interval to find the pressure-time curve gradient.
Figure 10:
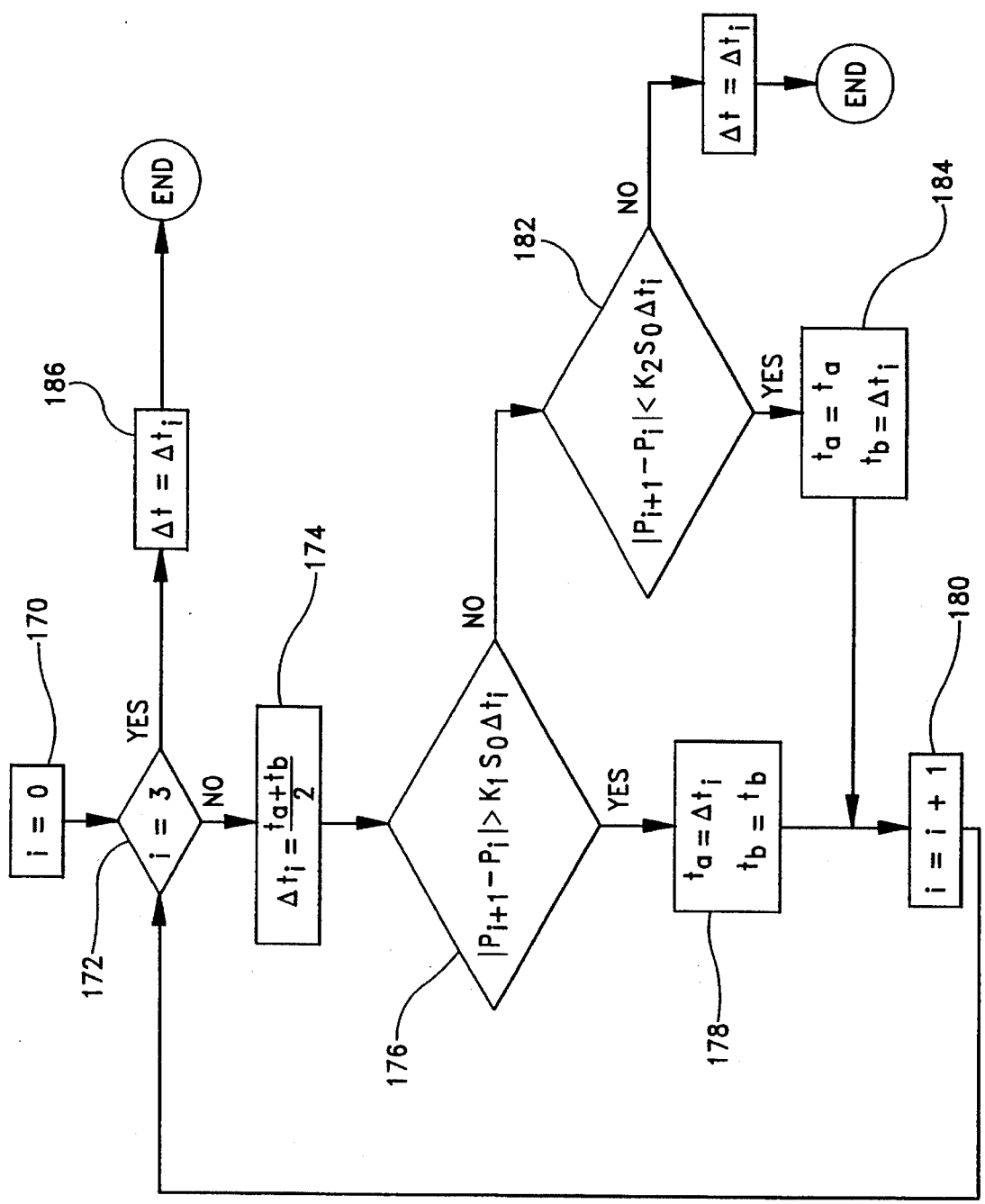
FIG. 10 is a flow chart representing the time interval optimization process to find the pressure-time curve gradient.

The optimal value for $\Delta t$ is achieved by application of the algorithm represented in FIGS. 9 and 10. Initially, the interval in which $\Delta t$ lies is established by means of the algorithm represented on FIG. 9. It has been observed experimentally that only three iterations are necessary to establish the interval.

A meter "i" is first set to zero (step 150 on FIG. 9). An initial value of $\Delta t$ is established in the preferred exemplified embodiment ($\Delta t_0 = 1$ minute). If less than two iterations have been done (i.e., i≠2 step 152), the pressure variation $\Delta P$ (i.e., $P_{i+1} - P_i$) in an interval $\Delta t$ between $t_i$ and $t_{i+1}$ is determined. The absolute value of the pressure difference is compared to $K_1 S_0 \Delta t_i$, using the values determined above (step 154). If the absolute value of $\Delta P_i$ is greater than $K_1 S_0 \Delta t_i$, then $\Delta t$ for the next time interval, $\Delta t_{i+1}$ is doubled (i.e., $\Delta t_{i+1} = 2\Delta t_i$) (step 156) and the meter "i" is increased by 1 (step 158), taking the algorithm for the next time interval. After three iterations (i.e., i=2), the value of $\Delta t_i$ is modified to $\Delta t$ (step 160), since the time interval is sufficiently large. If the absolute value of $\Delta P$ is no greater than $K_1 S_0 \Delta t$, then a time interval $[t_a; t_b]$ is determined by modifying values as follows (step 162):

$$t_a = \Delta t_{i-1}$$

$$t_a = 0 \text{ if } i = 0$$

$$t_b = \Delta t_i$$

The system then progresses to optimize $\Delta t$ for small time intervals according to a process called "process by dichotomy" represented in FIG. 3.

A counter "i" is set at zero (step 170). Empirically, it is observed that a maximum of four iterations are necessary to obtain a satisfactory optimization of $\Delta t$ independent of the flow rate. If less than four iterations have been done (step 172), $\Delta t$ for a particular interval is fixed at $(t_a + t_b)/2$ (i.e., the mean of the interval established above (step 174)). If the absolute value of $\Delta P$ ($P_{i+1} - P_i$) for this interval is greater than $K_1 S_0 \Delta t_i$ (step 176), the interval is modified again as follows (step 178):

$$t_a = \Delta t_i$$

$$t_b = t_b$$

and the counter is increased by 1 (step 180). The process continues the iteration until four iterations have been done.

If the absolute value of $\Delta P$ in any interval is no greater than $K_1 S_0 \Delta t_i$, then this value is compared to $K_2 S_0 \Delta t_i$ (step 182). If the absolute value of $\Delta P$ is less than $K_2 S_0 \Delta t_i$, then the interval is again determined as follows (step 184):

$$t_a = t_a$$

$$t_b = \Delta t_i$$

The counter is increased (step 180) and the iteration process is continued.

If the absolute value of $\Delta P$ is no less than $K_2 S_0 \Delta t_i$, then $\Delta t$ has been optimized and the time interval $\Delta t$ becomes $\Delta t_i$. The algorithm stops at that point.

In any case, after four iterations (i.e., i=3), $\Delta t$ becomes $\Delta t_i$ (step 186) and the algorithm stops.

We claim:

1. Process for the detection of obstructions in a perfusion line, the process being characterized by the fact that it comprises the steps consisting of:

choosing a gradient constant;

measuring a first pressure in the perfusion line;

measuring a second pressure in the perfusion line after a time interval;

subtracting the first pressure from the second pressure to obtain a first pressure difference;

comparing the first pressure difference to the gradient constant; and generating a signal if the first pressure difference exceeds or is equal to the gradient constant.

2. Process according to claim 1, characterized by the fact that it also comprises the steps consisting of:

measuring a second pressure in the diffusion line after a first time interval;

subtracting the first pressure from the second pressure to obtain a first pressure difference;

comparing the first pressure difference to the gradient constant;

measuring a third pressure after a second time interval;

subtracting the second pressure from the third pressure to obtain a second pressure difference;

comparing the second pressure difference to the gradient constant; and generating a signal if the first pressure difference and the second pressure difference exceed the gradient constant.

3. Process according to claim 1, characterized by the fact that the gradient constant is a function of the flow rate.

4. Process according to claim 1, characterized by the fact that the gradient constant is directly proportional to the flow rate.

5. Process according to claim 2, characterized by the fact that the first and second time intervals are essentially equal.

6. Process according to claim 2, characterized by the fact that it comprises steps consisting of:

comparing the first pressure difference to the gradient constant;

comparing the second pressure difference to the gradient constant; and generating the signal only if the first and second pressure differences both exceed the gradient constant.

7. Process according to claim 1, characterized by the fact that it also comprises a step with automatic modification of the time interval in inverse proportion to the fluid flow rate in the perfusion line.

8. Process according to claim 1, characterized by the fact that it also comprises a step with automatic adjustment of the time interval in response to a noise on the perfusion line.

9. Process according to claim 8, characterized by the fact that the time interval is automatically increased to reduce the influence of noise on the perfusion line.

10. Process according to claim 1, characterized by the fact that it also comprises a step with comparison of the first pressure difference to a constant and with adjustment of the first time interval if the first pressure difference exceeds the constant.

11. Process according to claim 10, characterized by the fact that the adjustment step comprises an increase in the first time interval.

12. Process according to claim 10, characterized by the fact that the constant is deduced from the gradient constant.

13. Process according to claim 10, characterized by the fact that the constant is the gradient constant multiplied by a scale change factor.

14. Process according to claim 13, characterized by the fact that the scale change factor is deduced empirically.

15. Process according to claim 1, characterized by the fact that it also comprises a step where the first pressure difference is compared to a constant and where the time interval is automatically adjusted if the first pressure difference is less than the constant.

16. Process according to claim 15, characterized by the fact that the adjustment step comprises a reduction of the time interval.

17. Process according to claim 1, characterized by the fact that it also comprises an optimization step for the first time interval.

18. Process according to claim 17, characterized by the fact that the optimization step uses a process by dichotomy.

19. Process according to claim 18, characterized by the fact that the optimization step comprises iteration steps to establish an initial time interval by comparing the first pressure difference to a constant.

20. Process according to claim 18, characterized by the fact that the optimization step comprises a time interval increase step if the absolute value of the first pressure difference exceeds a first constant and a time interval reduction step if the absolute value of the first pressure difference is less than a second constant.

21. Process according to claim 20, characterized by the fact that the time interval increase step comprises the doubling of the first time interval.

22. Process according to claim 20, characterized by the fact that the time interval reduction step comprises the step of dividing the first time interval by two.

* * * * *